(12) United States Patent
Kang

(10) Patent No.: US 10,603,347 B2
(45) Date of Patent: Mar. 31, 2020

(54) PHARMACEUTICAL COMPOSITION FOR PREVENTION OR TREATMENT OF LIVER DISEASE

(71) Applicant: Han Eun Kang, Seoul (KR)

(72) Inventor: Han Eun Kang, Seoul (KR)

( * ) Notice: Subject to any disclaimer, the term of this patent is extended or adjusted under 35 U.S.C. 154(b) by 0 days.

(21) Appl. No.: 16/070,858

(22) PCT Filed: Sep. 26, 2017

(86) PCT No.: PCT/KR2017/010653
§ 371 (c)(1),
(2) Date: Jul. 18, 2018

(87) PCT Pub. No.: WO2018/062819
PCT Pub. Date: Apr. 5, 2018

(65) Prior Publication Data
US 2019/0022161 A1  Jan. 24, 2019

(30) Foreign Application Priority Data

Sep. 30, 2016  (KR) .................. 10-2016-0126045

(51) Int. Cl.
| | |
|---|---|
| *A61K 36/00* | (2006.01) |
| *A61K 36/41* | (2006.01) |
| *A61K 9/19* | (2006.01) |
| *A61P 1/16* | (2006.01) |
| *A23L 33/105* | (2016.01) |
| *A61K 9/00* | (2006.01) |

(52) U.S. Cl.
CPC ............ *A61K 36/41* (2013.01); *A23L 33/105* (2016.08); *A61K 9/0056* (2013.01); *A61K 9/19* (2013.01); *A61P 1/16* (2018.01); *A23V 2002/00* (2013.01); *A61K 2236/19* (2013.01); *A61K 2236/51* (2013.01)

(58) Field of Classification Search
None
See application file for complete search history.

(56) References Cited

U.S. PATENT DOCUMENTS 5,445,835 A * 8/1995 Vedamuthu .......... A23C 9/1236
426/42

FOREIGN PATENT DOCUMENTS

| KR | 10-0604354 | 7/2006 |
|---|---|---|
| KR | 10-2014-0065184 | 5/2014 |
| KR | 20140131024 A * | 11/2014 |
| KR | 10-2015-0080871 | 7/2015 |
| KR | 10-1754040 | 7/2017 |

OTHER PUBLICATIONS

International Search Report dated Jan. 11, 2018 for PCT/KR2017/010653.
Ahn, Hee-Young et al., "Improvement Effect of Fermented Orostachys Malacophyllus against Orotic Acid-inducted Fatty Liver Model Rats", Journal of Life Science, Aug. 2015, vol. 25, No. 8, pp. 917-924.

* cited by examiner

*Primary Examiner* — Qiuwen Mi

(57) ABSTRACT

The present invention relates to a pharmaceutical composition for preventing or treating liver disease, and more particularly, to a pharmaceutical composition capable of preventing or treating liver disease by using a fermented product of *Orostachys japonicus*, and a method of producing the same.

9 Claims, 8 Drawing Sheets

PHARMACEUTICAL COMPOSITION FOR PREVENTION OR TREATMENT OF LIVER DISEASE

This application claims the priority of Korean Patent Application No. 10-2016-0126045, filed on Sep. 30, 2016 in the KIPO (Korean Intellectual Property Office), the disclosure of which is incorporated herein entirely by reference. Further, this application is the National Stage application of International Application No. PCT/KR2017/010653, filed Sep. 26, 2017, which designates the United States and was published in Korean. Each of these applications is hereby incorporated by reference in their entirety into the present application.

TECHNICAL FIELD

The present invention relates to a pharmaceutical composition for preventing or treating a liver disease, and more particularly, to a pharmaceutical composition capable of preventing or treating liver disease by using a fermented product of *Orostachys japonicus*, and a method for producing the same.

BACKGROUND ART

The liver is an organ that plays an important role in defending the whole body from toxins introduced from the outside and taking charge of the metabolism of the ex-vivo substance. That is, it performs diverse kinds of functions such as converting various kinds of ingested nutrients into a form necessary for the living body and synthesizing various kinds of substances for life sustenance such as albumin, and biotransformation of xenobiotics into an easy-to-excrete state. As in vivo materials which are introduced into a body pass through the liver, the liver is more likely to be exposed to many toxic substances than nutrients and is more likely to be damaged than other organs. The liver has an excellent liver regeneration ability and it is fully recovered to some damage. However, if sustained damage is caused by excessive stress, smoking, exposure to chemicals due to environmental pollution, alcohol and virus infections, stop of bile secretion, and so on, not only the functions of a liver will be deteriorated, but also a part of the liver tissue will be completely destroyed. As a result, the damaged parts cannot be recovered to a normal state. Finally, a liver fibrosis may lead to fatal liver cirrhosis, and a liver cirrhosis may develop into a liver cancer. In addition, a liver disease is not diagnosed at the initial stage because it does not show serious pains or self-awareness symptoms, but it is not found until the end of the term. Therefore, it is impossible to treat a liver cancer at the appropriate time and accordingly, the mortality rate is accordingly high. In spite of seriousness of a liver disease, there is no effective treatment for a liver disease.

In the case of hepatitis caused by hepatitis virus, an antiviral drug is being used. However, there is a problem that the side effects are very serious. In recent years, the remarkably effective treatments have not been developed for a liver disease due to the increasing toxic substances caused by alcohol and environmental pollution. Therefore, there is an urgent need to develop a drug that may treat and prevent liver damage while maintaining the structure and the functions of a liver tissue.

On the other hand, the *Orostachys japonicus* is a perennial herbaceous plant with a dicotyledonous rosales crassulaceae, which is called as *Orostachys japonicus*, and it has been recorded that the oriental herb has a tremendous effect for anti-cancer effect, fever, geothermal, eczema and burn. It is known to be particularly effective for breast cancer, pancreatic cancer, bone marrow cancer, esophageal cancer, uterine cancer, lymph node cancer, stomach cancer, colon cancer, hypertension, hypotension, blood circulation, diabetes, paralysis, arthritis, constipation, vomiting and various adult diseases.

As the components present in the *Orostachys japonicus*, triterpenoids such as friedelin, epifriedlanol, glutinone and glutinol; sterol-based substances such as β-sisterol and campesterol; flavonoids such as fatty acid esters, camperol and quercetin; and aromatic acids such as 4-hydroxybenzoic acid and 3,4-dehydroxybenzoic acid and gallic acid. In recent years, studies on the treatment of various kinds of diseases using the *Orostachys japonicus* are actively and briskly under way.

In the case of *Orostachys japonicus*, 90~95% of the water is included. Thus, in order to expect the widely-known efficacy, it should be taken in an excessive amount, but it is impossible for patients who have much difficulties in digesting even the adequate amount of *Orostachys japonicus* because the digestive function is actually reduced to take excessive doses. Therefore, it will be necessary to comprehensively study the method to increase the effective component and to improve the convenience of administration of a drug.

DISCLOSURE OF THE INVENTION

Technical Problem

The present invention has been made to solve the above-mentioned problems of the prior art. Therefore, it is an object of the present invention to provide a pharmaceutical composition for effectively preventing or preventing liver disease by using a fermented product of *Orostachys japonicus*.

Another object of the present invention is to provide a method for producing a composition for preventing or treating liver disease, which may increase the effective component of *Orostachys japonicus* through a simple and easy process and enhance convenience of administration.

Technical Solution

According to one embodiment of the present invention, there is provided a pharmaceutical composition for preventing or treating liver disease comprising a fermented product of *Orostachys japonicus* as an effective component.

In the present invention, a method for producing the fermented product of the above-mentioned *Orostachys japonicus* is as follows.

First of all, *Orostachys japonicus* is prepared, is dried at a temperature of 30 to 50° C. for 24 to 72 hours, and then pulverized if necessary.

A solvent may be added to the dried and pulverized product of the above-mentioned *Orostachys japonicus* in order to obtain an *Orostachys japonicus* suspension. Here, the type of the solvent is not particularly limited, but it is preferable to use distilled water to carry out the fermentation process at a later time. Also, the amount of the solvent to be added is not particularly limited, but a solvent may be added so that the dried and pulverized product of *Orostachys japonicus* in the suspension may be contained in an amount of 5 to 20 w/v %, 5 to 15 w/v %, or 5 to 10 w/v %.

In the present invention, the above-mentioned *Orostachys japonicus* suspension is cultured using an enzyme or a culture solution of fermentation strain. However, it is preferable that fermentation is carried out using a culture solution of fermentation strain in order to maximize antioxidant or anti-inflammatory effects by increasing the effective component of *Orostachys japonicus*. It is more preferable that a fermentation process using an enzyme may be carried out, and then a fermentation process may be carried out using a culture solution of fermentation strain.

In the present invention, as the enzyme used in the fermentation of *Orostachys japonicus*, one or more substances selected from the group consisting of cellulase, hemicellulase and amyloglucosidase may be employed. Preferably, an enzyme mixed with a cellulase, a hemicellulase, and an amyloglucosidase at a weight ratio of 0.5 to 1.5:0.5 to 1.5:0.5 to 1.5 may be used.

In the present invention, the cellulase may be (1,4-(1,3: 1,4)-β-D-glucan 4-glucano-hydrolase), and preferably, cellulclast produced by Novozyme company may be used, but it is not limited thereto.

In the present invention, HTec2 of Novozyme is preferably used as the hemicellulase, but the present invention is not limited thereto.

In the present invention, the enzyme is added to the suspension of the above-mentioned *Orostachys japonicus*, and is fermented for 12 to 48 hours, 12 to 36 hours, or for 24 to 36 hours to obtain a primary fermented product.

In the present invention, the amount of the added enzyme is not particularly limited. For example, the enzyme may be added in an amount of 5 to 20%, 5 to 15%, or 5 to 10% in terms of volume for the total volume of the suspension of *Orostachys japonicus*.

When the primary fermented product as described above is obtained in the present invention, the secondary fermented product may be obtained by secondary fermentation using a culture solution of fermentation strain.

In the present invention, one or more selected from a group consisting of *Lactobacillus hilgardii*, *Leuconostoc mesenteroides*, *Pediococcus acidilactici* and *Saccharomyces cerevisiae* may be used as the fermentation strain. However, it is preferable to use one or more selected from *Leuconostoc mesenteroides* and *Pediococcus acidilactici* as the fermentation strain. It is more preferable to use *Pediococcus acidilactici*, so that the therapeutic effect of liver disease may be enhanced remarkably by increasing the effective component of *Orostachys japonicus*.

In addition, in the present invention, the culture solution of the fermentation strain may further include a juice medium or a vegetable juice medium to improve the activity of the fermentation strain. Here, the type of the juice medium is not particularly limited. For example, it may be obtained from fruits such as citrus fruits, grapes, apples, mangos, oranges, pineapples, brambles, strawberries, peaches, blueberries or pomegranates, but is not limited thereto and may be a puree of fruits. Furthermore, kinds of the vegetable juice are not particularly limited, and Embodiments thereof include a juice such as carrot, tomato, cabbage and the like, but the present invention is not limited thereto, and it may be a vegetable puree.

The fruit juice and the vegetable juice may be obtained by grinding a fruit or vegetable with a mixer or the like, and further squeezing as needed. It is preferable that such fruit juice and vegetable juice is suitably concentrated, and the concentrate is used as it is, or is diluted with distilled water to a suitable concentration.

The above-mentioned fruit juice and vegetable juice may be used alone or in combination according to the purpose. In addition, the puree of fruit or vegetables may be obtained by enzymatic treatment under ultra-high pressure (for example, 100 MPa) and contains abundantly vegetable fibers. Enzymes used in this enzyme treatment may be appropriately selected depending on the type of fruit or vegetable.

Furthermore, in the present invention, the culture solution may contain a fermentation strain by an amount of $10^6$ to $10^9$ cells/ml, $10^6$ to $10^8$ cells/ml or $10^6$ to $10^7$ cells/ml.

In the present invention, the fermented product may be obtained by adding the culture solution of the fermentation strain to the suspension of the above-mentioned *Orostachys japonicus* and then, through a static culturing for 3 to 10 days at 30 to 40° C.

However, the addition amount of the culture solution is not particularly limited, but may be preferably 0.05 to 0.5% by weight, 0.05 to 2% by weight, or 0.05 to 0.1% by weight for the total weight of the suspension.

When the secondary fermented product is obtained as described above in the present invention, the secondary fermented product may be freeze and dried if necessary. Here, the conditions for performing a lyophilization process are not particularly limited but may be carried out at −60 to 30° C. for 6 to 50 hours, for example. Preferably, it may be performed for 1 to 3 hours at −40 to −20° C., for 1 to 3 hours at −20 to −10° C., for 3 to 5 hours at −5 to 0° C., for 1 to 3 hours at 10 to 20° C., and for 1 to 3 hours at 20 to 30° C.

In the present invention, the formulation of the fermented product of the above-mentioned *Orostachys japonicus* is not particularly limited, and may be, for example, a liquid fermented product or a solid fermented product of *Orostachys japonicus*. The formulation of the fermented product of the above-mentioned *Orostachys japonicus* may be variously adjusted depending on the taste of the patient to be administered or the purpose of use.

The fermented product of *Orostachys japonicus* which is obtained as above according to the present invention effectively inhibits the production of iNOS, COX-2 and TNF-α and its gene expression by inhibiting transcription of NF-κB and AP-1 in the nucleus of liver cells. Therefore, it is possible to prevent or treat a liver damage due to antioxidant and anti-inflammatory responses.

The liver disease to be prevented or treated in the present invention may be selected from the group consisting of autoimmune liver disease, drug-induced liver disease, alcoholic liver disease, infectious liver disease and congenital metabolic liver disease. Preferably, it may be an infectious liver disease.

On the other hand, Lipopolysaccharide (LPS) stimulates production of inflammatory substances and thus, acute liver damage will occur, which causes fatty liver and a weight ratio of liver tissue to a body weight will increase. In the human body, fat accounts for about 5% of the liver, and a phenomenon that much more fat is accumulated is called fatty liver. When the fatty liver is getting worse and worse, it turns into hepatitis and cirrhosis, and then it reaches liver cancer.

Therefore, it is the most preferable that the pharmaceutical composition of the present invention may be used for the prevention or treatment of acute liver damage mediated by lipopolysaccharide or fatty liver caused because of it.

In the present invention, the content of the fermented product of *Orostachys japonicus* in the pharmaceutical composition is not particularly limited but may be in the range of 0.1 to 50% by weight for the total weight of the composition.

In the present invention, the term "prevention" may include any action that inhibits or suppresses or delays liver disease using the pharmaceutical composition of the present invention without limitations.

Further, in the present invention, the term "treatment" may include without limitation any action which improves or alleviates liver disease using the pharmaceutical composition of the present invention.

The pharmaceutical compositions of the present invention may further comprise suitable carriers, excipients or diluents according to conventional methods. As the Embodiments of carriers, excipients and diluents that may be included in the pharmaceutical composition of the present invention, lactose, dextrose, sucrose, sorbitol, mannitol, xylitol, erythritol, maltitol, starch, acacia rubber, alginate, gelatin, calcium phosphate, calcium silicate, cellulose methyl cellulose, microcrystalline cellulose, polyvinyl pyrrolidone, methylhydroxybenzoate, propylhydroxybenzoate, talc, magnesium stearate, mineral oil, and so forth may be enumerated. But, they are not limited to the above Embodiments.

In addition, the pharmaceutical composition according to the present invention may be formulated in a form of powders, granules, tablets, capsules, oral formulations such as suspensions, emulsions, syrups and aerosols, external preparations, suppositories, and a form of a sterile injectable solution. In detail, when formulating the composition, it may be prepared by using a diluent or an excipient such as a filler, an extender, a binder, a wetting agent, a disintegrant, or a surfactant, which are now commonly used. Solid formulations for oral administration include tablets, pills, powders, granules, capsules and the like. Such solid preparations may be prepared by mixing at least one or more excipients, for example, starch, calcium carbonate, sucrose, lactose, gelatin, and the like together with the pharmaceutical composition of the present invention. In addition to simple excipients, lubricants such as magnesium stearate and talc may also be used. Embodiments of liquid formulations for oral use may include suspensions, solutions, emulsions, and syrups. In addition to water and liquid paraffin, which are commonly used as simple diluents, various excipients such as wetting agents, sweeteners, aromatics, preservatives and so on may be used. Formulations for parenteral administration may include sterile aqueous solutions, non-aqueous solutions, suspensions, emulsions, lyophilized preparations and suppositories. Embodiments of non-aqueous solvents and suspensions may include propylene glycol, polyethylene glycol, vegetable oils such as olive oil, and injectable esters such as ethyl oleate. As the suppository base, witepsol, macrogol, tween 61, cacao paper, laurin paper, glycerogelatin and the like may be used.

The route of administration of the pharmaceutical compositions according to the present invention may be, but is not limited to, oral, intravenous, intramuscular, intraarterial, intramedullary, intrathecal, intracardiac, transdermal, subcutaneous, intraperitoneal, intranasal, hypogloss or rectal. Oral or parenteral administration is preferred. The term "parenteral" as used herein includes subcutaneous, intradermal, intravenous, intramuscular, intraarticular, intrasynovial, intrasternal, intrathecal, intralesional and intracranial injection or infusion techniques. The pharmaceutical compositions of the present invention may also be administered in the form of suppositories for rectal administration.

The pharmaceutical composition of the present invention may vary depending on various factors including the activity of the used specific compound, age, weight, general health, sex, diet, time of administration, route of administration, rate of excretion, drug combination and the severity of the particular disease to be prevented or treated. The dosage of the pharmaceutical composition may vary depending on the condition of the patient, the body weight, the degree of disease, the type of drug, the route of administration, and the period of time, but may be appropriately selected by a person skilled in the art and dosage of administration may range from 0.0001 to 50 mg/kg or 0.001 to 50 mg/kg. The administration may be carried out once a day or divided into several doses. The amount of dosage does not in any way limit the scope of the invention. The pharmaceutical composition according to the present invention may be formulated into pills, sugarcoated pills, capsules, solutions, gels, syrups, slurries, and suspensions.

According to another embodiment of the present invention, the present invention is related to a food composition which comprises a fermented product of *Orostachys japonicus* as an effective component for preventing or improving liver disease.

In the food composition of the present invention, the above-mentioned fermented product of *Orostachys japonicus* may be referred to if there are no points which are inconsistent with the disclosure of the pharmaceutical composition of the present invention.

The food composition of the present invention may be prepared in the form of various foods such as beverage, gum, tea, vitamin complex, powder, granule, tablet, capsule, confection, rice cake, bread and the like. Since the food composition of the present invention is composed of a plant extract having little toxicity and side effects, it may be safely used even for a long time for preventive purposes.

When the composition of the present invention is contained in the food composition, the amount thereof may be added in a proportion of 0.1 to 50% of the total weight.

Here, when the food composition is prepared in a beverage form, there are no particular limitations other than those containing the food composition in the indicated ratios and may contain various flavors or natural carbohydrates such as ordinary beverages as an additional ingredient. That is, the natural carbohydrates may include monosaccharides such as glucose, disaccharides sucrose such as fructose, the common sugars such as polysaccharide, dextrin, cyclodextrin and the like, and sugar alcohols such as xylitol, sorbitol, erythritol and the like. As the Embodiments of the above-mentioned flavors, natural flavors (such as tau martin, *stevia* extract (for example, rebaudioside A and glycyrrhizin)) and synthetic flavors (for example, saccharin and aspartame) and so on may be enumerated.

In addition, the food composition of the present invention may include a flavoring agent such as various nutrients, vitamins, minerals(electrolytes), synthetic flavors and natural flavors; colorants, pectic acid and its salts, alginic acid and its salts, organic acid, protective colloid thickeners, a pH adjusting agent, a stabilizer, an antiseptic, a glycerin, an alcohol, a carbonating agent used in a carbonated drink, and the like.

These components may be used independently or in combination. The proportion of such an additive may be selected in the range of 0.1 to about 50 weight parts per 100 weight parts of the composition of the present invention.

Advantageous Effects

In the present invention, the fermented product of *Orostachys japonicus* can inhibit transcription of NF-κB and AP-1 in the nucleus of liver cells, thereby effectively inhibiting the production of iNOS, COX-2 and TNF-α and their gene expression. In addition, because of these antioxidant and anti-inflammatory responses, liver damage may be effectively prevented or treated.

MODE FOR CARRYING OUT THE INVENTION

Figure 1:
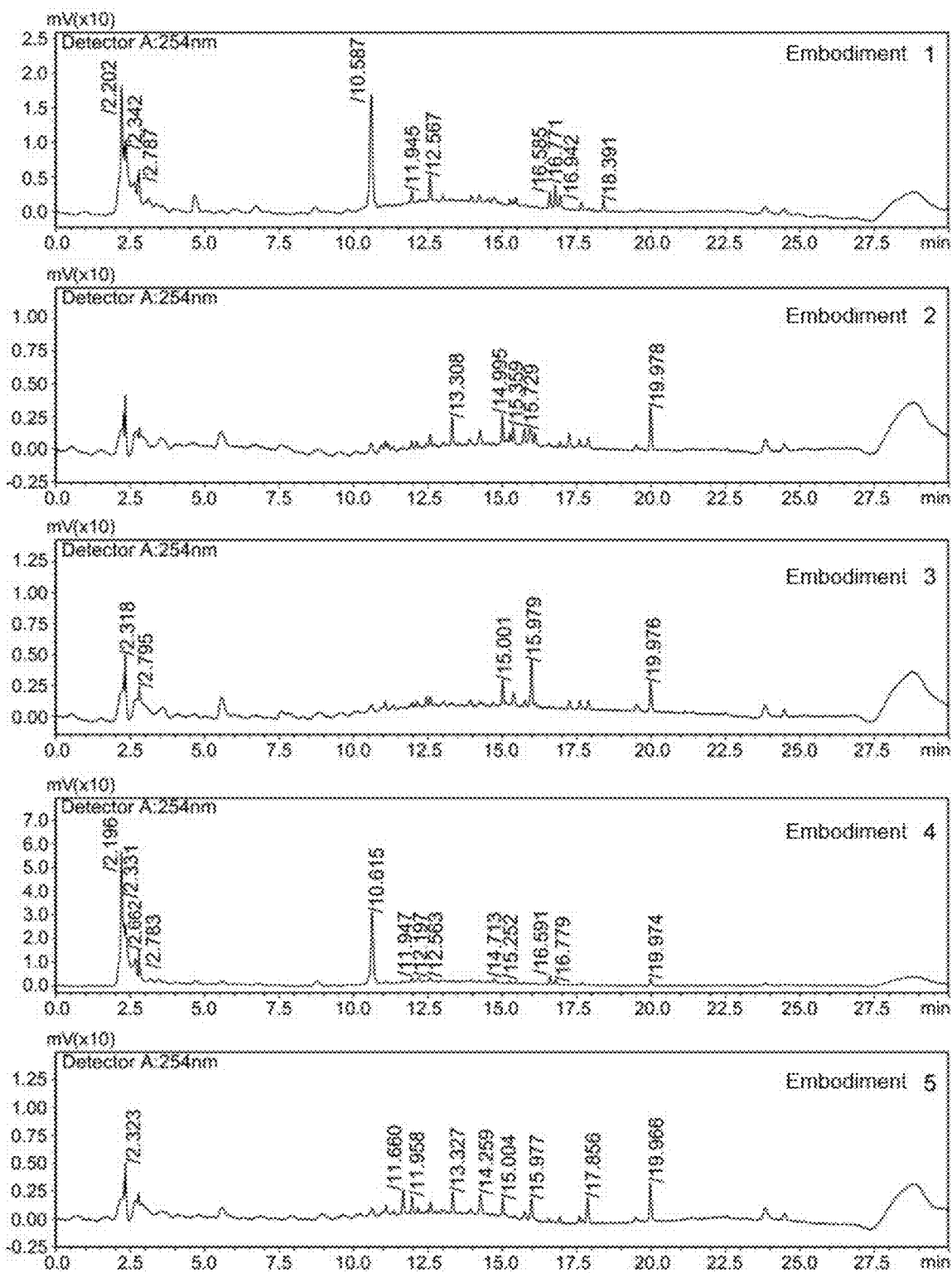
FIG. 1 shows the result of UPLC component analysis on the fermented product of *Orostachys japonicus* in Embodiments 1 to 5 in Evaluation Example 4.

Hereinafter, preferred embodiments of the present invention will be described. However, the embodiments of the present invention may be modified in various types, and the present invention is not limited to the embodiment described as above. Further, the embodiments of the present invention are provided to more fully explain the present invention to those skilled in the art having an average knowledge.

[Preparation Example 1] Preparation of Materials

1. Preparation of Medicines

Orostachydis Herba is purchased from Bareun oriental medicine shop (Seoul, Republic of Korea).

2. Preparation of Enzymes

As the enzyme used for the first fermentation, a mixture of Cellulclast (Novozymes, Denmark), HTec2 (Novozymes, Denmark) and amyloglucosidase (1:1:1) provided by the Fusion Chemistry Research Team of Korea Research Institute of Chemical Technology was used.

3. Preparation of Culture Solution of Fermentation Strain

As the culture solution to be used for the second fermentation, each of four kinds of fermentation strains such as *Lactobacillus hilgardii*, *Leuconostoc esenteroides*, *Pediococcus acidilactici* and *Saccharomyces cerevisiae* was fermented by liquid fermentation, and then the strain suspension was prepared by adding a juice medium so that the concentration of the strain may be $10^7 \sim 10^8$ cells/ml. However, all of the reagents used for the culture of microorganisms were purchased from Difco (Difco Laborator, Detroit, Mich. USA). The juice medium was added to the strain culture solution so that the concentration of the strain may be $10^7 \sim 10^8$ cells/ml.

4. Preparation of Other Reagents and Materials

LPS derived from *Escherichia coli* (serotype O55:B5, L2880), 1,1-diphenyl-2-picrylhydrazyl (DPPH), 2,2'-azino-bis 3-ethyl-benzothiazoline-6-sulfonic acid (ABTS) was purchased from Sigma aldrich (MO, USA). Nitrocellulose membrane was purchased from Amersham GE Healthcare (Little Chalfont, UK), and phenylmethylsulfonyl fluoride (PMSF), nuclear factor-kappa B(NF-κBp65), inducible nitric oxide synthase (iNOS), cyclooxygenase-2(COX-2), tumor necrosis factor alpha (TNF-α), histone and β-actin and secondary antibodies were purchased from Santa Cruz Biotechnology (Santa Cruz, 1) were purchased from Cell sinaling (CA, USA). Activator protein-1 (AP-1) was purchased from Cell sinaling (CA, USA). Protease inhibitor mixtures, DMSO and ethylenediamine tetraacetic acid (ethylenediaminetetraacetic acid, EDTA) was purchased from Wako Pure Chemical Industries, Ltd. (Osaka, Japan). In addition, 2',7'-dichlorofluorescein diacetate (DCFH-DA) and dihydrorhodamine 123 were obtained from Molecular Probes (Eugene, Oreg., USA), and western blot detection reagents were purchased from GE Healthcare. BCA protein assay kit for protein quantification was purchased from Thermo Scientific (Rockford, Ill., USA).

[Embodiments 1 to 5] Preparation of Liquid Fermented Product of *Orostachys japonicus*

1. Drying and Pulverization of *Orostachys japonicus*

After washing the purchased *Orostachys japonicus*, it was dried at 40° C. for 3 days at a low temperature using a dryer (HDG-222, HyunDaeEnetech, HwaSung, Korea) and then ultrasonically pulverized into fine powders using an ultrafine particle grinder (Jet Mill, Ducksan, Siheung, Republic of Korea).

2. Primary Fermentation 5 g of dried *Orostachys japonicus* powder was weighed, placed in five containers, and 45 ml of sterilized distilled water was added thereto to suspend the solid content to 10 w/v %. 0.5 ml of the complex enzyme solution prepared in advance was added to a container containing each suspension, and the mixture was fermented overnight.

3. Secondary Fermentation 0.5 ml of the culture solution was inoculated into each container containing the primary fermented product as shown in the following Table 1 and then, the product was processed through a static culture in a constant temperature incubator (Joyotec, Daejeon, Republic of Korea) fixed at a temperature 30° C., and a shaking incubator (Jeio Tech, Daejeon Republic of Korea). Samples were intermittently shaken during a fermentation process.

TABLE 1

| ITEM | Primary Fermentation | Secondary Fermentation |
| --- | --- | --- |
| Embodiment 1 | ○ | — |
| Embodiment 2 | ○ | *Lactobacillus hilgardii* |
| Embodiment 3 | ○ | *Leuconostoc mesenteroides* |
| Embodiment 4 | ○ | *Pediococcus acidilactici* |
| Embodiment 5 | ○ | *Saccharomyces cerevisiae* |

[Embodiments 6 to 10] Preparation of a Solid Fermented Product of *Orostachys japonicus*

Five kinds of liquid fermented products were prepared in the same manner as in Embodiments 1 to 5, and then, the liquid fermented products were lyophilized at −30° C. for 120 minutes, at −15° C. for 120 minutes, at 0° C. for 240 minutes, at 15° C. by using the freeze-drier (LYOPH-PRIDE 20R, Ilshin BioBase, Republic of Korea).

[Evaluation Example 1] pH Analysis

The pH was measured to evaluate whether the fermentation of the fermented product was proceeded successfully or not in Embodiments 2 to 5. The results are shown in Table 2 as below. However, the pH was measured using a pH Shear type of Waterproof company.

TABLE 2

| | pH Fermentation Time (day) | | |
| --- | --- | --- | --- |
| Item | 1 | 2 | 3 |
| Embodiment 2 | 7.11 | 6.44 | 6.35 |
| Embodiment 3 | 7.03 | 7.04 | 7.75 |
| Embodiment 4 | 3.95 | 4.35 | 4.75 |
| Embodiment 5 | 7.24 | 6.65 | 6.84 |

As shown in Table 2, it is observed that the pH is changing as the fermentation time elapses. In the case of Embodiments 2 and 5, the strains used in fermentation were acid-producing strains. Thus, as the time passes by, it is observed that the pH of the fermented product decreased, whereas in Embodiments 3 and 4, the pH was increased.

[Evaluation Example 2] DPPH (1,1-diphenyl-2-picrylhydrazyl) Radical Scavenging Activity In order to evaluate the antioxidant ability of the fermented product obtained in Embodiments 1 to 5, the fermented product was diluted 100-fold and then analyzed for DPPH radical scavenging activity. Specifically, the electron donating ability was measured by the DPPH free radical scavenging method. DPPH is a free radical, and the solution is deep violet, which binds to the antioxidant in the sample and becomes neutralized (reduced) and as a result, the solution becomes transparent. Thus, DPPH is used to measure the amount of antioxidant (radical scavenging activity) material contained in the sample.

100 μl of each of the fermented samples of Embodiments 1 to 5 was added to 100 μl of a solution in which 60 μl of DPPH solution had been dissolved in ethanol, and the mixture was reacted at room temperature for 30 minutes. After measuring the absorbance at 540 nm using this reaction solution, the electron donating ability was calculated by the equation (A). The results are shown in Table 3 as below.

$$\text{Radical Scavenging Activity (\%)} = \{(OD_{control} - OD_{sample})/OD_{control}\} \times 100 \quad \text{[Equation (a)]}$$

$OD_{control}$: (control) absorbance when a sample is not included.

$OD_{sample}$: (control) absorbance when a sample is included.

TABLE 3

| ITEM | Embodiment 1 | Embodiment 2 | Embodiment 3 | Embodiment 4 | Embodiment 5 |
| --- | --- | --- | --- | --- | --- |
| DPPH radical scavenging activity (%) | 97.54 ± 0.18 | 40.68 ± 1.24*** | 26.43 ± 1.05*** | 94.96 ± 0.21 | 29.12 ± 1.62*** |

***means $p < 0.001$.

As shown in Table 3, all of embodiments 1 to 5 exhibited a high DPPH radical scavenging ability, and in particular, embodiments 1 and 3 showed very high DPPH radical scavenging ability. Embodiment Example 2 showed the next highest DPPH radical scavenging ability. Thus, it can be seen that the fermented product of *Orostachys japonicus* according to the present invention has excellent antioxidant ability.

[Evaluation Example 3] ABTS (2,2'-azinobis-3-ethylbenzothiazoline-6-sulfonic Acid) Radical Scavenging Ability In order to evaluate the antioxidant ability of the fermented products obtained in Embodiments 1 to 5, the fermented product was diluted 100-fold and analyzed for ABTS radical scavenging ability. Specifically, 7 mm ABTS and 2.45 mm potassium persulfate were dissolved in distilled water and stored for 12 hours while preventing lights from penetrating into the distilled water. The reaction solution was adjusted to 0.70±0.02 absorbance at 415 nm using ethanol. Then, 5 μl of the fermented samples of Embodiments 1 to 5 was added to 95 μl of ABTS, was allowed to react for 15 minutes, and the absorbance was measured at 415 nm. The absorbance was calculated by the equation (b), and the results are shown in Table 4 as below.

$$\text{Radical Scavenging Activity (\%)} = \{(OD_{control} - OD_{sample})/OD_{control}\} \times 100 \quad \text{[Equation(b)]}$$

$OD_{control}$: (control) absorbance when a sample is not included.

$OD_{sample}$: (control) absorbance when a sample is included.

TABLE 4

| ITEM | Embodiment 1 | Embodiment 2 | Embodiment 3 | Embodiment 4 | Embodiment 5 |
|---|---|---|---|---|---|
| ABTS Radical Scavenging Activity (%) | 79.50 ± 2.43 | 40.20 ± 0.18*** | 33.83 ± 1.76 | 83.12 ± 2.59*** | 43.12 ± 0.69*** |

***means $p < 0.001$.

As shown in Table 4, Embodiment 1 to 5 exhibited high ABTS radical scavenging ability, and in particular, Embodiment 4 showed very high ABTS radical scavenging ability. Embodiment 1 had the next highest ABTS radical scavenging ability. Thus, it can be seen that the fermented product of *Orostachys japonicus* according to the present invention has excellent antioxidant ability.

[Evaluation Example 4] Component Analysis

In order to analyze the components contained in 1 ml of the fermented product obtained in Embodiment 1 to 5, the fermented product was analyzed using a UPLC coupled to the mass spectrometer of an ESI source from Waters. For the separation of components, ACQUITY UPLC BEH C18 (2.1×150.0 mm, 1.7 μm) column was employed. The mobile phase was forced to be flowed under the conditions shown in Table 5 under a gradient solvent condition using water containing 0.1% formic acid and acetonitrile. The column was maintained at 40° C., the flow rate was 0.18 ml/min and the injection volume was set to 3.0 μl. For quantitative analysis, ACQUITY TQD MS was used for detection in cation and anion modes. For the MS detection, the conditions concerning the capillary voltage (3.3 kV), extract voltage (3 V), interface temperature (120° C.), RF lens (0.3V), desolvation temperature (300° C.), desolvation gas (600 L/50 L/h) and collision gas (0.14 ml/min) were set and the multiple reaction monitoring(MRM) mode was applied for quantitative analysis. The components contained in 1 ml of the fermented product of Embodiment 1 to 5 were analyzed and the results are shown in Table 6 as below. The fermented *Orostachys japonicus* was indicated through analysis of the contents of quercetin and kaempferol. That is, it means that tr was detected, but the quantitative value was not significant.

TABLE 5

| TIME | MOBILE PHASE | |
|---|---|---|
| (MINUTE) | A % (0.1% formic acid) | B % (Acetonitrile) |
| 10 | 90 | 10 |
| 30 | 40 | 60 |
| 40 | 30 | 70 |
| 45 | 30 | 70 |
| 50 | 90 | 10 |

TABLE 6

| ITEM | Rutin | isoquercitrin | kaempferol-3-O-rutinoside | quercitrin | quercetin | kaempferol |
|---|---|---|---|---|---|---|
| Embodiment 1 | No peak | No peak | No peak | No peak | 5.38723 | 9.94246 |
| Embodiment 2 | No peak | No peak | No peak | No peak | No peak | No peak |
| Embodiment 3 | No peak | No peak | No peak | No peak | No peak | No peak |
| Embodiment 4 | No peak | No peak | No peak | No peak | No peak | No peak |
| Embodiment 5 | No peak | No peak | No peak | No peak | No peak | No peak |

As shown in Table 6 and FIG. 1, as a result of precisely analyzing the components of the rutin, isoquercitrin, kaempferol-3-O-rutinoside, quercitrin, quercetin and kaempferol contained in the liquid fermented product of *Orostachys japonicus* obtained in Examples 1 to 5 The contents of kaempferol-3-O-rutinoside, quercitrin, quercetin and kaempferol were analyzed, it was observed that the content of quercetin was 5.38 in the fermented product of Example 1, and the content of kaempferol was 9.94.

[Evaluation Example 5] Improvement Effects of Acute Liver Damage Caused by LPS (Lipopolysaccharide)

The test groups were classified into total five groups such as a normal group to which no treatment was given to ICR mice (6 weeks old, male), control group treated with LPS, and an administration group wherein the fermented products obtained in Embodiments 1, 3 and 4 were orally administered to the control group at a dose of 200 mg/kg once a day for 8 days. Then, 6 mice were assigned to each group.

Samples were suitably and orally administered to each dose for 8 days. On the 9th day of the experiment, 20 mg/kg of LPS was intraperitoneally injected for 24 hours, and then anesthetized with ethyl ether. Subsequently, the blood was collected from the heart, and serum was immediately separated using a centrifugal separator. Then, the liver was then perfused with saline (0.9% NaCl, pH 7.4) and the organ weight was measured and immediately stored at −80° C. until analysis.

Figure 2:
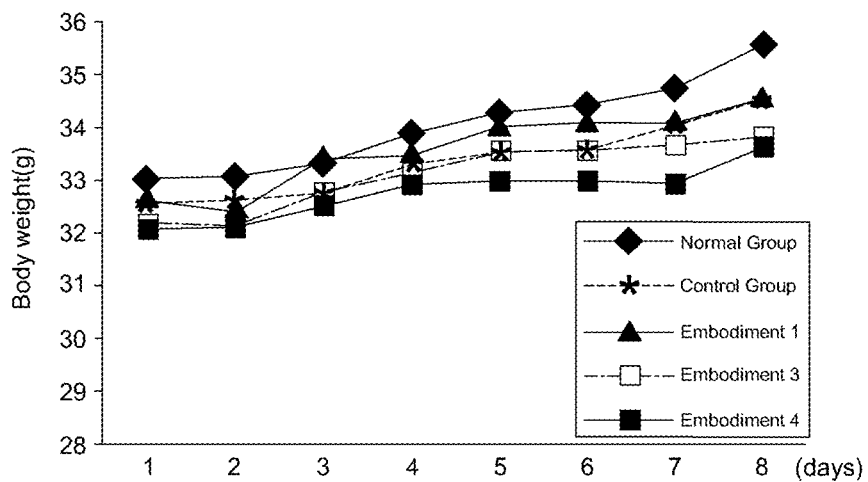
FIG. 2 is a graph showing change in body weight according to each treatment in an acute liver damage mouse model by LPS in Evaluation Example 5.
Figure 3:
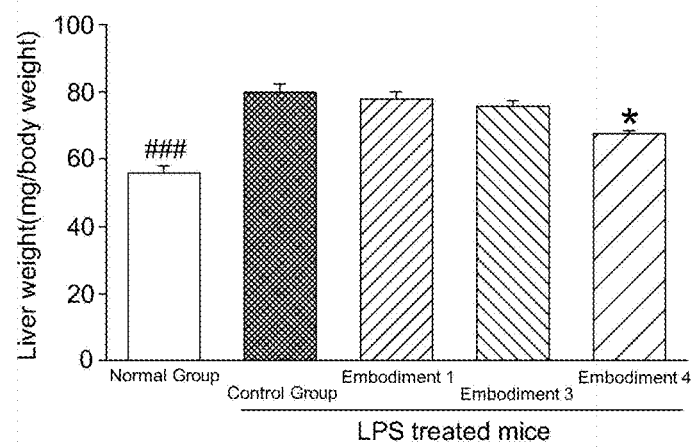
FIG. 3 is a graph showing change in weight ratio of liver tissue for mouse body weight according to each treatment in an acute liver damage mouse model by LPS in Evaluation Example 5.

The body weight change and the dietary efficiency were measured during the 8-day dietary feeding period except for the adaptation period, and the results are shown in Table 7 and FIG. 2. The weight ratio of the liver tissue to the weight of the mouse was measured, and the results are shown in FIG. 3.

TABLE 7

| ITEM | Initial body weight (g) | Final Body weight (g) | Increase of body weight (g) | FER (%) |
|---|---|---|---|---|
| Normal group | 33.02 ± 0.54 | 35.56 ± 0.77 | 2.54 ± 0.33 | 0.16 ± 0.02 |
| Control group | 32.52 ± 0.37 | 34.50 ± 0.41 | 1.99 ± 0.14 | 0.14 ± 0.01 |
| Embodiment 1 | 32.62 ± 0.38 | 34.53 ± 0.51 | 1.92 ± 0.28 | 0.12 ± 0.02 |
| Embodiment 3 | 32.18 ± 0.50 | 33.83 ± 0.68 | 1.65 ± 0.28 | 0.10 ± 0.02 |
| Embodiment 4 | 32.08 ± 0.50 | 33.65 ± 0.46 | 1.57 ± 0.20 | 0.10 ± 0.01 |

As shown in Table 7 and FIG. 2, it was observed that the body weight is constantly increased in the normal group, the control group, and the administration group in which the fermented products of Embodiments 1, 3 and 4 are administered, as the time is passing by.

Also, as shown in FIG. 3, it was observed that the weight ratio of the liver tissue to the body weight of the control group is significantly increased as compared with the normal group. However, there is a tendency that the weight ratio is decreasing in the administration group to which the fermented products of Examples 1, 3 and 4 are administered. In particular, it was observed that when the fermented product of Example 4 was administered, it was significantly decreased compared to the control group.

Therefore, it can be seen that the pharmaceutical composition of the present invention inhibits the production of fatty liver due to the acute liver damage caused by LPS and helps to recover the liver function.

[Evaluation Example 6] Measurement of Serum ALT and AST

The blood collected from the mouse hearts of the normal group, the control group, and the administration group of Evaluation Example 5 was centrifuged at 4,000 rpm for 10 minutes in a centrifugal separator in order to obtain serum. The activity of alanine aminotransferase (ALT) and aspartate aminotransferase (AST) in serum was measured according to colorimetric analysis of a spectrophotometer while using a reagent kit manufactured by Reitman-Frankel method at 505 nm. The amount of serum per liter was measured according to an international unit (IU/L). The results are shown in FIGS. 4 and 5, respectively.

AST(aspartate aminotransferase/GOT(glutamic oxaloacetic transaminase)), ALT (alanine aminotransferase/GPT (glutamic pyruvate transaminase)) are enzymes related to a liver function, which is present in the mitochondria in the liver cells and is an enzyme that is released into the blood by the destruction of hepatocytes. In other words, AST and ALT are enzymes present in liver cells, and when hepatocytes are damaged, they are released into the blood and as a result, n blood levels will increase.

Figure 4:
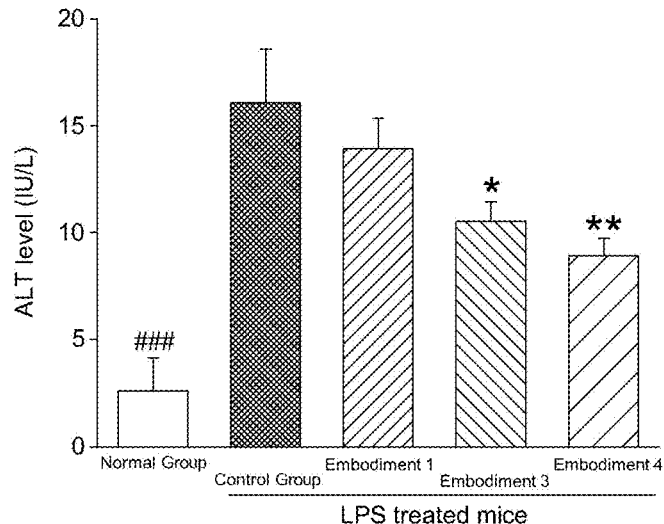
FIG. 4 is a graph showing the results of measurement of changes in ALT levels in serum according to each treatment in a mouse model of acute liver damage by LPS in Evaluation Example 6.

As shown in FIG. 4, ALT was significantly increased in the control group due to the destruction of the hepatocyte as compared with the normal group. However, in case of the group administered with the fermented products of Examples 1, 3 and 4, ALT was decreased as compared with the control group. In particular, when the fermented product of Examples 3 and 4 was administered, it can be seen that ALT was significantly decreased as compared with the control group.

Figure 5:
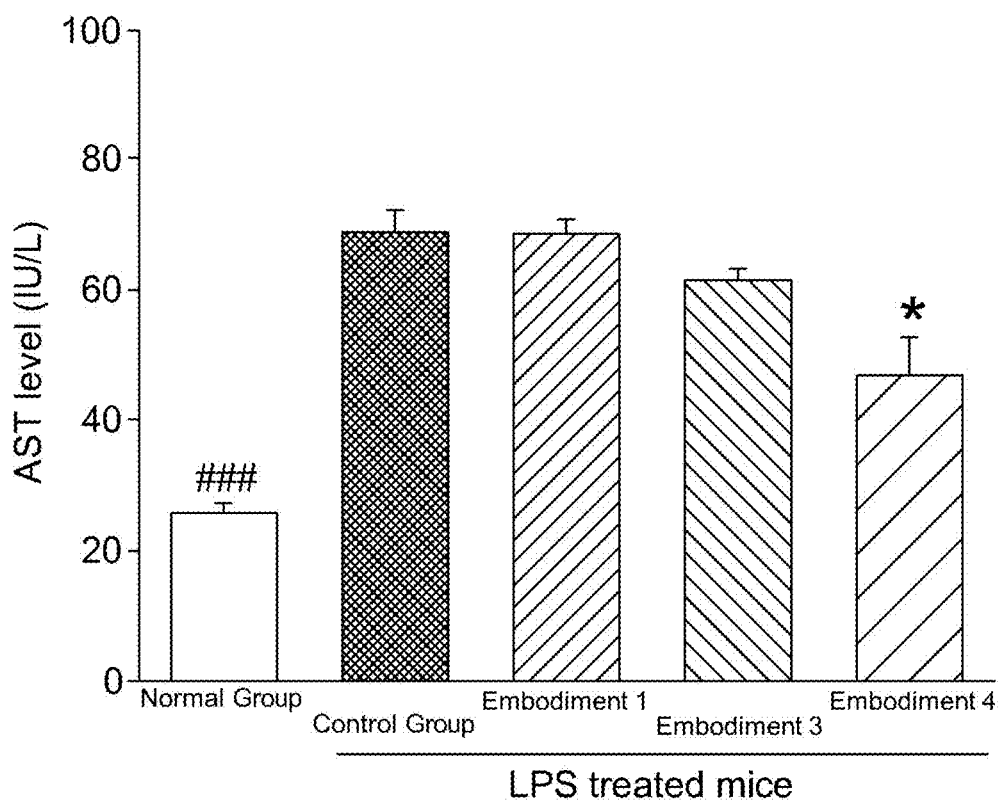
FIG. 5 is a graph showing the results of measurement of changes in AST levels in serum according to each treatment in a mouse model of acute liver damage caused by LPS in Evaluation Example 6.

As shown in FIG. 5, AST was significantly increased in the control group as compared to the normal group. However, in case of the group administered with the fermented products of Examples 1, 3, and 4, AST was decreased as compared with the control group. When the fermented products of Examples 3 and 4 were administered, it can be seen that the AST was significantly decreased as compared with the control group.

As described above, it can be understood that the pharmaceutical composition of the present invention may successfully recover liver damage induced by LPS and accordingly, it may be expected to exhibit excellent effects on liver diseases such as acute, chronic liver damage and fatty liver.

[Evaluation Example 7] Measurement of Active Oxygen Species (ROS)

Blood collected from the mouse hearts of normal group, control group and administration group of Evaluation Example 5 was centrifuged at 4,000 rpm for 10 minutes to obtain serum. Liver tissues were pulverized with 1 mM EDTA-50 mM sodium phosphate buffer (pH 7.4). In order to measure ROS in serum and liver tissues, 25 mM DCFH-DA was added and the calculated value was measured for 30 minutes using 530 nm emission wavelength and 485 nm excitation wavelength at every 10 minutes from 0 minutes using a fluorescence photometer, respectively. The results are shown in FIG. 6 (a) and FIG. 6 (b), respectively.

Figure 6:
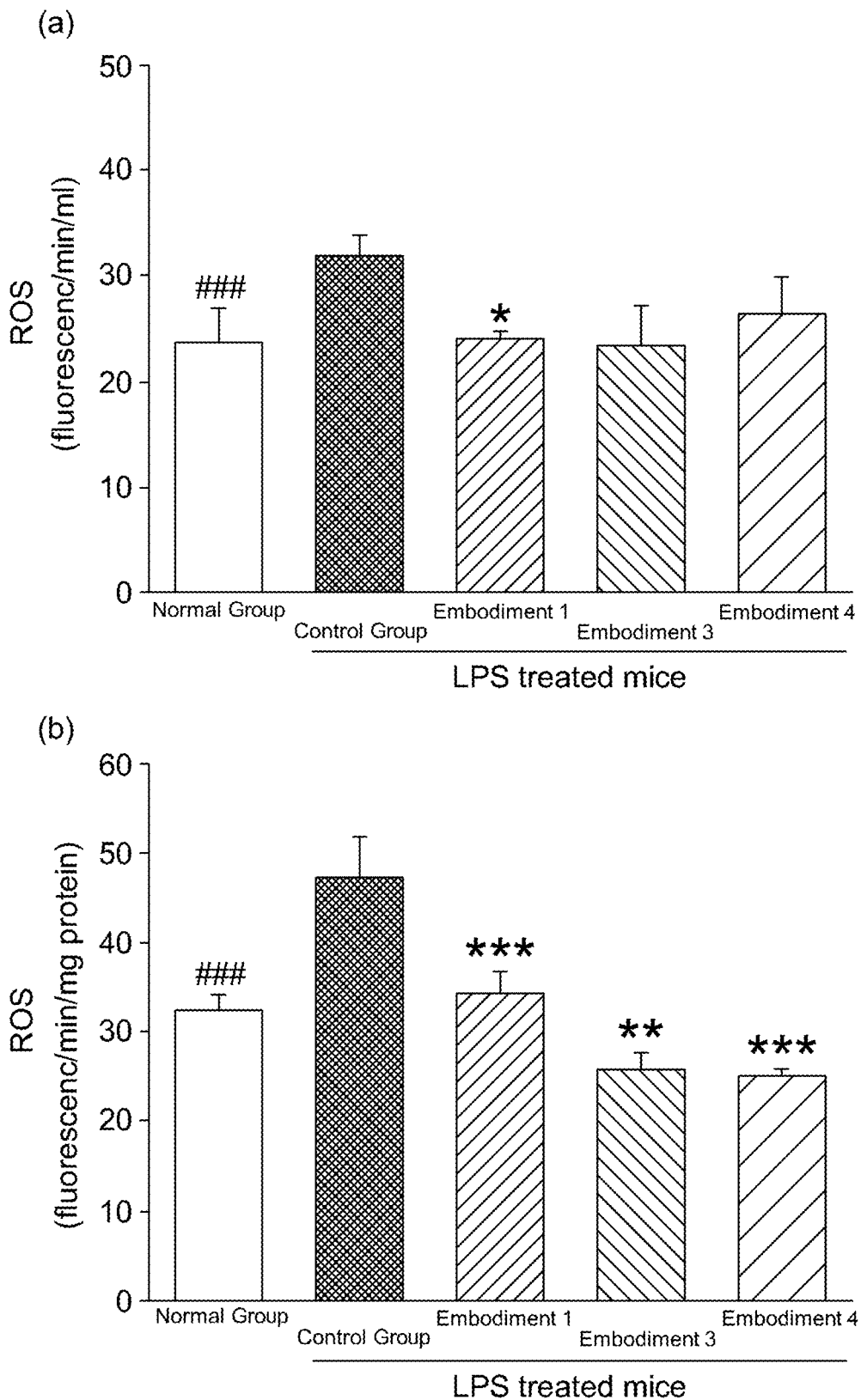
FIG. 6 is graphs showing changes in serum and liver ROS levels according to each treatment in the mouse model of acute liver damage by LPS in Evaluation Example 7.

As shown in FIG. 6, the biomarker of oxidative stress, that is, ROS, was measured as higher in the control group as compared with the normal group. However, when the fermented products of Embodiments 1, 3 and 4 were administered, it can be seen that the measured amount is reduced as compared with the control group. In particular, when the fermented products of Embodiments 1, 3 and 4 were administered to liver tissues, it can be observed that ROS was significantly decreased as compared with the control group.

Oxidative stress plays an important role in liver damage induced by LPS, and excessive production of ROS causes an antioxidant system imbalance and as a result, causes cellular damage. Therefore, ROS plays a major role in improving tissue damage. When the pharmaceutical composition according to the present invention is administered, it can be seen that ROS decreases in serum and liver tissue, and especially was significantly decreased in liver tissue. Therefore, it is to be understood that there is a tremendous effect in improving the liver damage.

[Evaluation Example 8] Western Blot

Buffer A supplemented with 100 mM Tris-HCl (pH 7.4), 5 mM Tris-HCl (pH 7.5), 2 mM $MgCl_2$, 15 mM $CaCl_2$, 1.5 M sucrose, 0.1 M DTT and protease inhibitor cocktail were added, the mixture was pulverized with a tissue grinder, and 10% NP-40 solution was added thereto in order to obtain cytoplasmic proteins between the mice of the normal group, the control group and the administration group in Evaluation Example 5. The mixture was allowed to stay on ice for 20 minutes and then, the supernatant containing cytoplasmic proteins was isolated through centrifugation at 12,000 rpm for 2 minutes.

In order to obtain the nucleoprotein, the mixture was rinsed twice in Buffer A supplemented with 10% NP-40, and 100 μl of buffer C (50 mM HEPES, 50 mM KCl, 0.3 mM NaCl, 0.1 mM EDTA, 1 mM DTT, 0.115 mM PMSF and 10% glycerol) was added. After re-floating, the vortex was performed 3 times every 10 minutes. After centrifugation at 12,000 rpm for 10 mins at 4° C., the supernatants containing nuclear proteins were obtained and stored frozen at −80° C., respectively.

In order to measure expression of iNOS, COX-2, TNF-α, β-actin and nuclear protein AP-1, NF-κB p65, and histone proteins, 10 μg of protein was subject to an electrophoresis process using 8-15% SDS-polyacrylamide gel, and the acrylamide gel was transferred to a nitrocellulose membrane. Each of the prepared membranes was treated with each primary antibody, reacted overnight at 4° C. overnight, and then washed five times with PBST every 6 minutes. The cells were reacted at room temperature for 1 hour with a secondary antibody (diluted 1:3000 with PBST) used for each primary antibody treated, and then washed 5 times with PBST every 6 minutes. In addition, the sensitized chemiluminescence (ECL) solution was exposed to GE Healthcare (Arlington Heights, Ill., USA) and sensitized to Sensi-Q2000 Chemidoc (Lugen Sci Co., Ltd., Seoul, Korea). After the protein expression was confirmed, the band was quantified using ATTO Densitograph Software (ATTO Corporation, Tokyo, Japan) program and the results were shown in FIG. 7 to FIG. 11.

Figure 7:
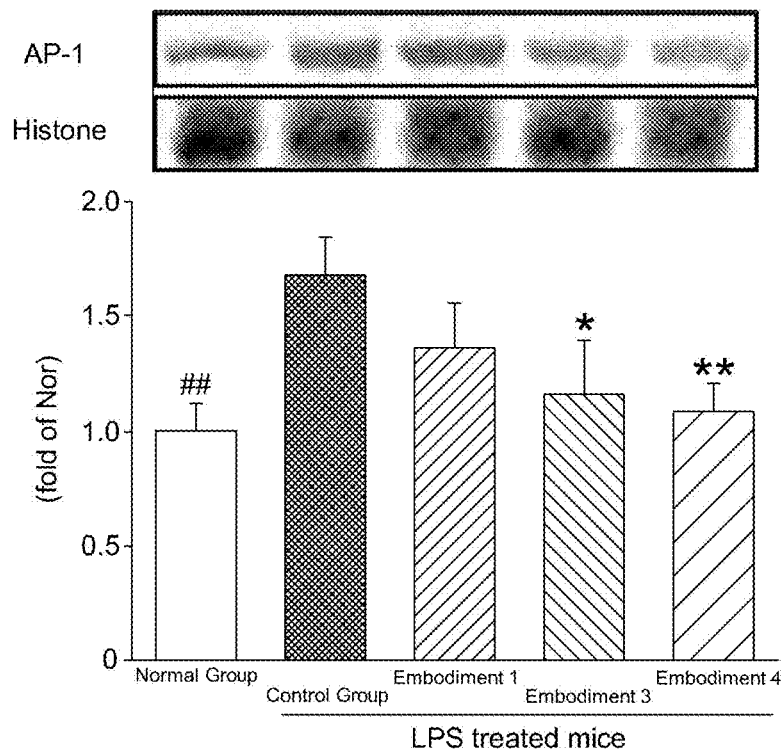
FIG. 7 is a graph showing changes in AP-1 expression level according to each treatment in an acute liver damage mouse model by LPS in Evaluation Example 8.
Figure 8:
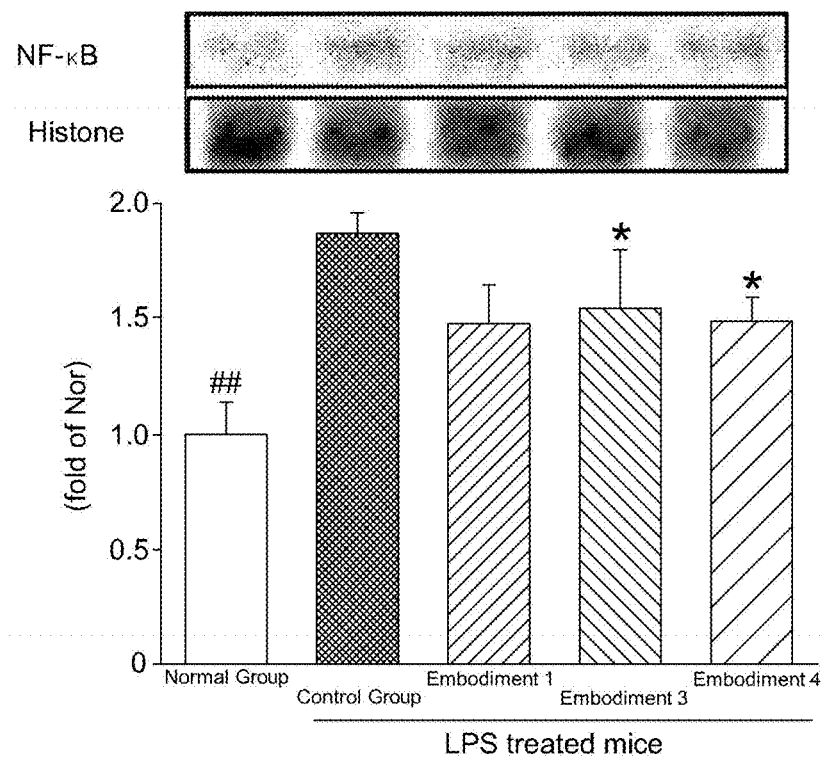
FIG. 8 is a graph showing changes in the amount of NF-κB p65 expression in each of the treatments in the mouse model of acute liver damage caused by LPS in Evaluation Example 8.

As shown in FIG. 7 and FIG. 8, as a result of measuring the expression levels of AP-1 and NF-κB p65, which are inflammatory mediators, the expression level of the control group was significantly increased as compared with that of the normal group, but it was observed that when the fermented products of Embodiments 1, 3 and 4 were administered, the expression level was significantly decreased as compared with the control group.

Figure 9:
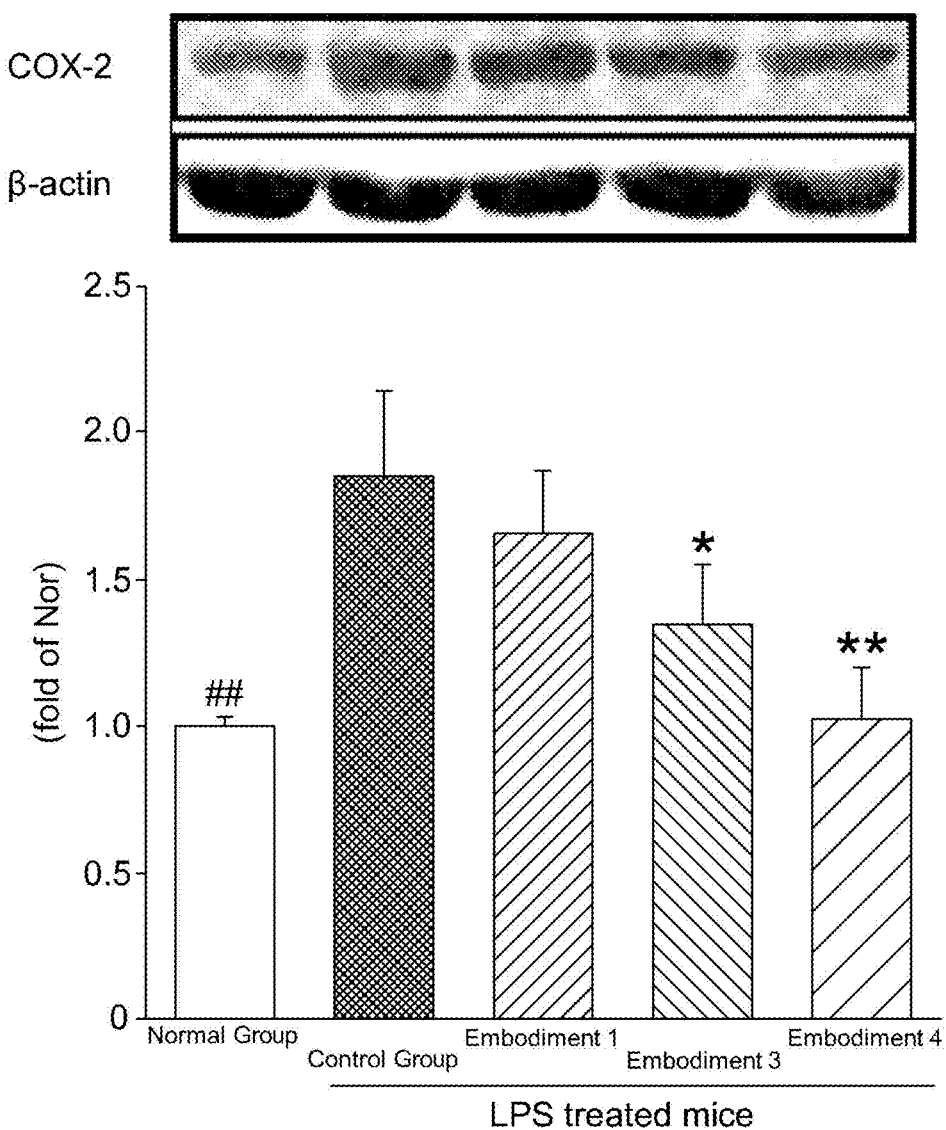
FIG. 9 is a graph showing changes in COX-2 expression level according to each treatment in an acute liver damage mouse model by LPS in Evaluation Example 8.
Figure 10:
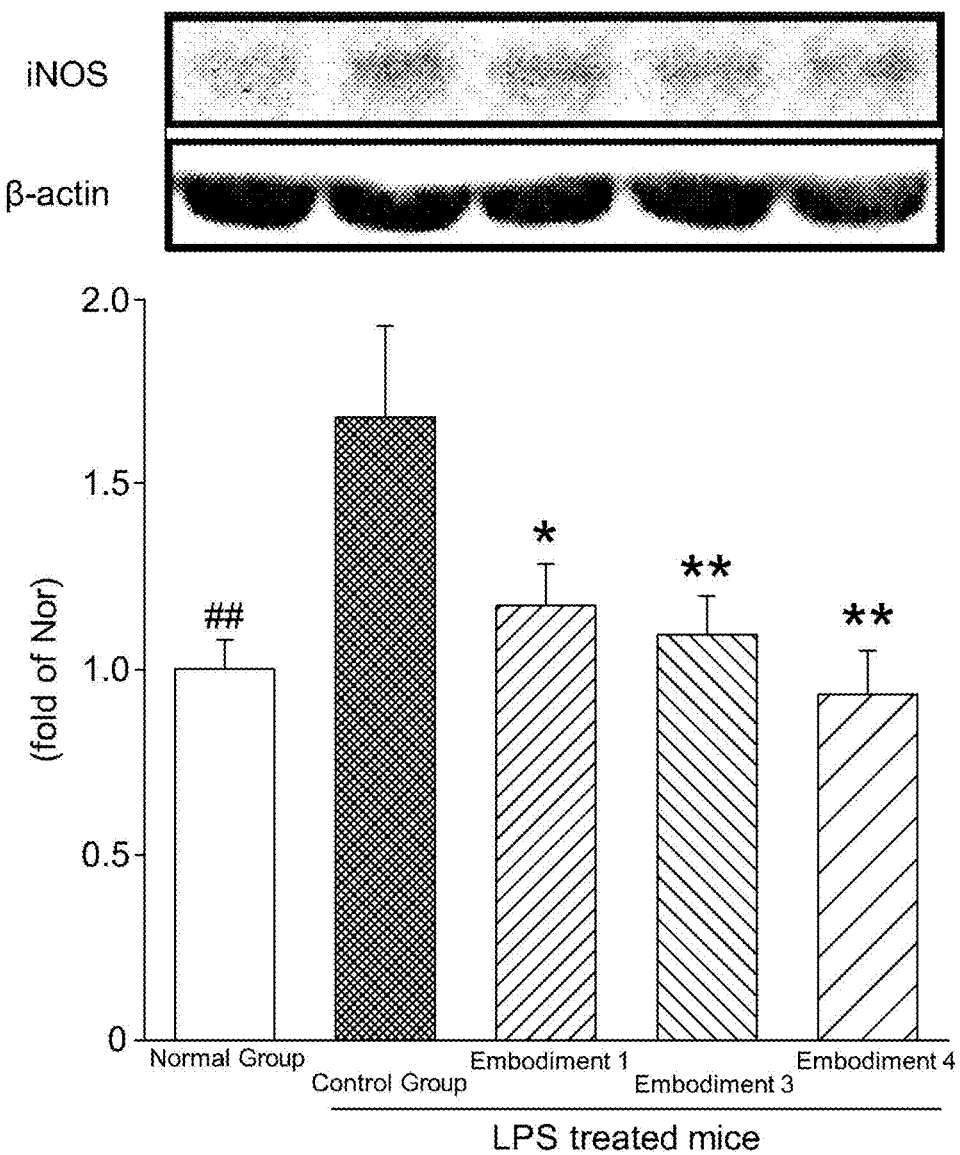
FIG. 10 is a graph showing changes in iNOS expression level according to each treatment in an acute liver damage mouse model by LPS in Evaluation Example 8.
Figure 11:
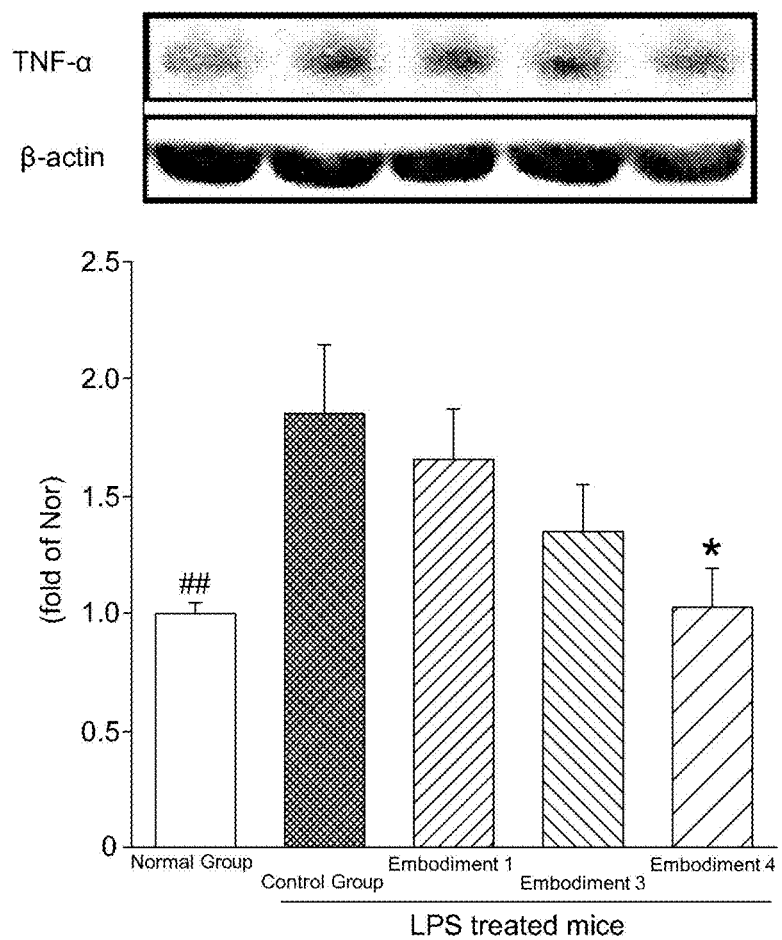
FIG. 11 is a graph showing the change in the amount of TNF-α expression according to each treatment in the mouse model of acute liver damage caused by LPS in Evaluation Example 8.

Further, as shown in FIGS. 9 to 11, as a result of measuring the expression level of COX-2, iNOS and TNF-α, the expression levels were significantly increased in the control group as compared with the normal group. However, when the fermented products of Embodiments 1, 3 and 4 were administered, it can be seen that the expression level was remarkably decreased as compared with the control group. Particularly, in connection with the case that the fermented products of Embodiments 3 and 4 were administered in the expression of COX-2; all of Embodiments 1, 3 and 4 in the expression of iNOS; and the case that the fermented product of Embodiment 4 was administered in the expression of TNF-α, it was observed that the expression level was significantly decreased as compared with the control group.

Through this experimentation, the pharmaceutical composition of the present invention may inhibit formation of inflammatory precursors through a signal transmission adjustment of NF-κB and AP-1.

[Evaluation Example 9] Tissue Analysis

The liver tissues of mice of the normal, control and administration groups of the above evaluation example 5 were extracted and were fixed in 10% neutral formalin for 18 hours or longer. Then, they were dehydrated and were paraffin-embedded to prepare 4 μm sections. Hematoxylin and eosin (H & E) staining was then performed and observed under an optical microscope. The results are shown in FIG. 12 (A)-(E).

Figure 12:
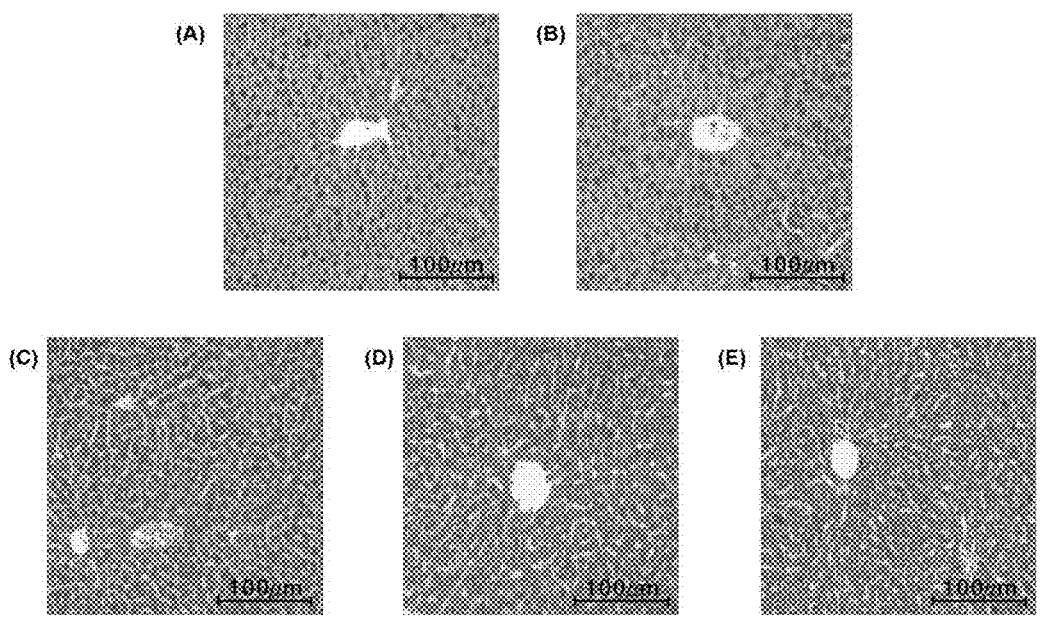
FIG. 12 is photographs of liver tissue which is observed under an optical microscope after each treatment in an acute liver damage mouse model by LPS in Evaluation Example 9.

As shown in FIG. 12, it was observed that the degree of inflammation around the blood vessels was increased in the control group (b) as compared with the normal group (a), and the appearance of the nucleus was remarkably reduced. However, in the fermented product-administered group (c) of Embodiment 1, the fermented product-administered group (d) of Embodiment 3, and the fermented product-administered group (e) of Embodiment 4, it was observed that the degree of inflammation around the blood vessels is decreased and the presence or absence of nucleus are distinctively identified.

In the above experiment according to the present invention, all values were expressed as mean±SEM. One-way analysis of variance (ANOVA) using SPSS (22.0 for Windows program is performed with significance level p-value <0.05.

INDUSTRIAL APPLICABILITY

Judging from the above results, it can be confirmed that the pharmaceutical composition of the present invention has significant effects on antioxidative and anti-inflammatory effects in connection with acute liver cell damage induced by LPS. Particularly, it can be seen that the fermented product (Embodiments 3 and 4) which has progressed to the secondary fermentation has much more excellent effects as compared with the primary fermented product (Embodiment 1). In particular, in the secondary fermentation, it can be seen that the fermented product (Example 4) using a strain of *Pediococcus acidilactici* has the most excellent and outstanding effect.

The invention claimed is:

1. A pharmaceutical composition comprising a fermented product of *Orostachys japonicus* as an effective component for prevention or treatment of a liver disease,
wherein the fermented product of *Orostachys japonicus* is obtained by firstly fermenting *Orostachys japonicus* with an enzyme and then fermenting secondarily with a culture solution of fermentation strain.

2. The pharmaceutical composition of the claim 1, wherein the enzyme is a mixture in which cellulase, hemicellulase, and amyloglucosidase are mixed.

3. The pharmaceutical composition of the claim 1, wherein the enzyme is a mixture in which cellulase, hemicellulase and amyloglucosidase are mixed according to a weight ratio of 0.5 to 1.5: 0.5 to 1.5: 0.5 to 1.5.

4. The pharmaceutical composition of the claim 1, wherein the fermentation strain includes more than one strains selected from a group consisting of *Lactobacillus hilgardii, Leuconostoc mesenteroides, Pediococcus acidilactici* and *Saccharomyces cerevisiae*.

5. The pharmaceutical composition of the claim 4, wherein the fermentation strain includes *Pediococcus acidilactici*.

6. The pharmaceutical composition of the claim 1, wherein a culture solution of the fermentation strain includes the fermentation strain in an amount of $10^6$ to $10^9$ cells/ml.

7. The pharmaceutical composition of the claim 1, wherein the fermented product is a lyophilizate.

8. The pharmaceutical composition of the claim 1, wherein the liver disease is selected from a group consisting of an autoimmune liver disease, a drug-induced liver disease, an alcoholic liver disease, an infectious liver disease, and a congenital metabolic liver disease.

9. A food composition comprising a fermented product of *Orostachys japonicus* as an effective component for preventing or improving a liver disease,
wherein the fermented product of *Orostachys japonicus* is obtained by firstly fermenting *Orostachys japonicus* with an enzyme and then fermenting secondarily with a culture solution of fermentation strain.

\* \* \* \* \*